United States Patent
Naka et al.

(10) Patent No.: US 6,624,193 B1
(45) Date of Patent: Sep. 23, 2003

(54) PREVENTIVE AND THERAPEUTIC AGENTS FOR EYE DISEASES

(75) Inventors: Hiroaki Naka, Kobe (JP); Kazuhito Kawabata, Mishima-gun (JP); Hideki Tokushige, Kobe (JP)

(73) Assignees: Ono Pharmaceutical Co., Ltd., Osaka (JP); Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/070,307
(22) PCT Filed: Sep. 5, 2000
(86) PCT No.: PCT/JP00/06014
§ 371 (c)(1),
(2), (4) Date: Apr. 2, 2002
(87) PCT Pub. No.: WO01/17527
PCT Pub. Date: Mar. 15, 2001

(30) Foreign Application Priority Data

Sep. 6, 1999 (JP) ............................................. 11-251538

(51) Int. Cl.⁷ ........................ A01N 37/02; A01N 37/12; A61K 31/22; A61K 31/195; C07C 69/00
(52) U.S. Cl. ........................ 514/546; 514/562; 514/604; 514/618; 514/619; 560/138; 560/142
(58) Field of Search .................. 514/546, 562, 514/604, 618, 619, 564; 560/138, 142

(56) References Cited

FOREIGN PATENT DOCUMENTS

| EP | 347168 | 12/1989 |
| EP | 0 519 354 | 12/1992 |
| EP | 539223 | 4/1993 |
| EP | 0 596 118 | 5/1994 |
| WO | 90/04409 | 5/1990 |

OTHER PUBLICATIONS

J. Cejkova et al., "Histochemical changes in the rabbit cornea and plasmin activity in the tear fluid during contact lens wear. Favourable influence of protease inhiitors (aprotinin, PC5, elastatinal)" Histochemistry, vol. 97, No. 1, 1992, pp. 69–76.

A. Spierer et al., "The effect of 2–mercaptoacetyl–L–phenylalanyl–L–leucine, a specific inhibitor of Pseudomonas aeruginos a elastase, on experimental Pseudomonas keratitis in rabbit eyes," Curr. Eye Res., vol. 3, No. 4, 1984, pp. 645–650.

Principles of Ambulatory Medicine, Fourth Edition. Barker et al, editors, pp. 943–952 and 1428–1431. Williams & Wilkins (1995).*

Webster's II New Riverside University Dictionary, p. 933, Houghton Mifflin Co. (1984).*

Gregory D. Sloop, et al., "Acute Inflammation of the Eyelid and Cornea in *Staphylococcus* Keratitis in the Rabbit," Invest. Ophthalmol. Vis. Sci., Feb. 1999, vol. 40, No. 2, pp. 385–391.

Jitka Čejková, "Histochemical Study of Leukocyte Elastase Activity in Alkali–Burned Rabbit Cornea," Opthalmic Research, 1997; 29, pp. 154–160.

O. Schmut, et al., "PMN–Elastase–Bestimmung in der Tränenflüssigkeit bei Ulcus corneae," Klin. Mbl. Augenheilk. 188, 1986, pp. 593–595.

Orhan Değer al., "Polymorphonuclear leukocyte elastase levels in patients with Behçet's disease," Clinica Chimica Acta, 236, 1995, pp. 129–134.

Nurettin Akyol, et al., "The importance of plasma polymorphonuclear (PMN) elastase determination in patients with uveitis," Acta Ophthalmol. Scandinavica, 1997, pp. 287–289.

Kiyohiro Tsutsui, et al., "Increased Plasma Granulocyte Elastase Levels in Behçet's Disease, " Journal of Rheumatology, 1998; 25:2, pp. 326–328.

J.P. Barletta et al., "Inhibition of Pseudomonal Ulceration in Rabbit Corneas by a Synthetic Matrix Metalloproteinase Inhibitor," Invest. Ophthalmol. Vis. Sci., 1996, vol. 37, No. 1, pp. 20–28.

* cited by examiner

Primary Examiner—Richard L. Raymond
Assistant Examiner—Zachary C. Tucker
(74) Attorney, Agent, or Firm—Wenderoth, Lind & Ponack, L.L.P.

(57) ABSTRACT

The present invention provides a prophylactic and therapeutic medicament for ophthalmic diseases, especially ophthalmic inflammatory diseases and corneal ulcer, comprising as an active ingredient a compound represented by the formula (I):

(I)

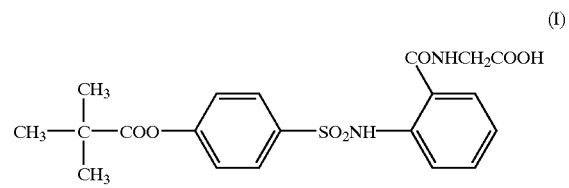

or a pharmacologically acceptable salt or hydrate thereof.

27 Claims, 9 Drawing Sheets

Days after endotoxin infusion

PREVENTIVE AND THERAPEUTIC AGENTS FOR EYE DISEASES

This application is a 371 of PCT/JP00/06014 filed Sep. 5, 2000.

TECHNICAL FIELD

The present invention relates to a prophylactic and therapeutic medicament for ophthalmic diseases having a leukocyte (neutrophil)-derived elastase inhibitory activity.

BACKGROUND OF THE INVENTION

JP-B 5-81586 and JP-A 5-194366 (corresponding to EP-A 539223) disclose a compound represented by the formula (I):

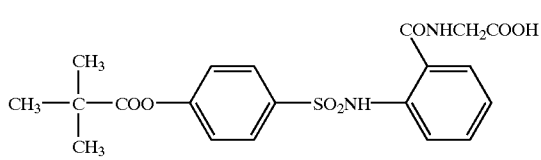

(hereinafter referred to as a compound of Formula (I)) and a salt or hydrate thereof, which has a human neutrophil-derived elastase inhibitory activity and is effective for preventing and treating diseases such as pulmonary emphysema, atherosclerosis and rheumatoid arthritis.

On the other hand, the ophthalmologic field also involves various diseases relating to leukocytes and their elastases. For example, ophthalmic infections, corneal traumas, corneal ulcers and uveitis may be mentioned in an ophthalmic infection, the cellular infiltration of leukocytes results in an intraocular abscess [Invest. Ophthalmol. Vis. Sci., 40, 385–391 (1999)]. An alkaline trauma (erosion) which is one of corneal traumas allows leukocytes to, be infiltrated into corneal stromal cells at an early stage of the alkaline erosion, two to three weeks after which the elevation of leukocyte elastase activity is observed [Ophthalmic. Res., 29, 154–160 (1997)]. Also in a case of corneal ulcers, a corneal wound or detachment results in the infiltration of leukocytes into a corneal stroma, which leads to the release or secretion of a protease such as an elastase or collagen [Klin. Monatsbl. Augenheilkd, 188, 593–595 (1986)]. An uveitis, especially Behcet's disease, was reported to undergo an increase in a plasma leukocyte elastase [Clin. Chim. Acta 236:129–134 (1995), Acta, Ophthalmol. Scand. 75:287–289 (1997), J.Reumatol. 25: 326–328 (1998)]. While leukocytes or their elastases were reported to be involved in the ophthalmic diseases mentioned above, no actual effect of the administration of an elastase inhibitor was reported.

While in JP-A 5-221872 (corresponding to EP-A 519354) and JP-A 6-509232 (corresponding to EP-A 596118), a microbe-derived substance having human leukocyte elastase inhibitory activity is described generally to be useful as a prophylactic and therapeutic medicament against a corneal scar tissue formation or a fibroblast proliferation [eye solidification (burn, mechanical or chemical damage, keratoconjunctivitis) and the like], it was not administered actually to verify its effect, and is different totally from a compound of Formula (I).

OBJECTS OF THE INVENTION

An objective of the present invention is to develop a prophylactic and therapeutic medicament for ophthalmic diseases containing as an active ingredient a compound of Formula (I).

This objective as well as other objectives and advantages of the present invention will be explained hereinafter with reference to the attached drawings.

SUMMARY OF THE INVENTION

Figure 1:
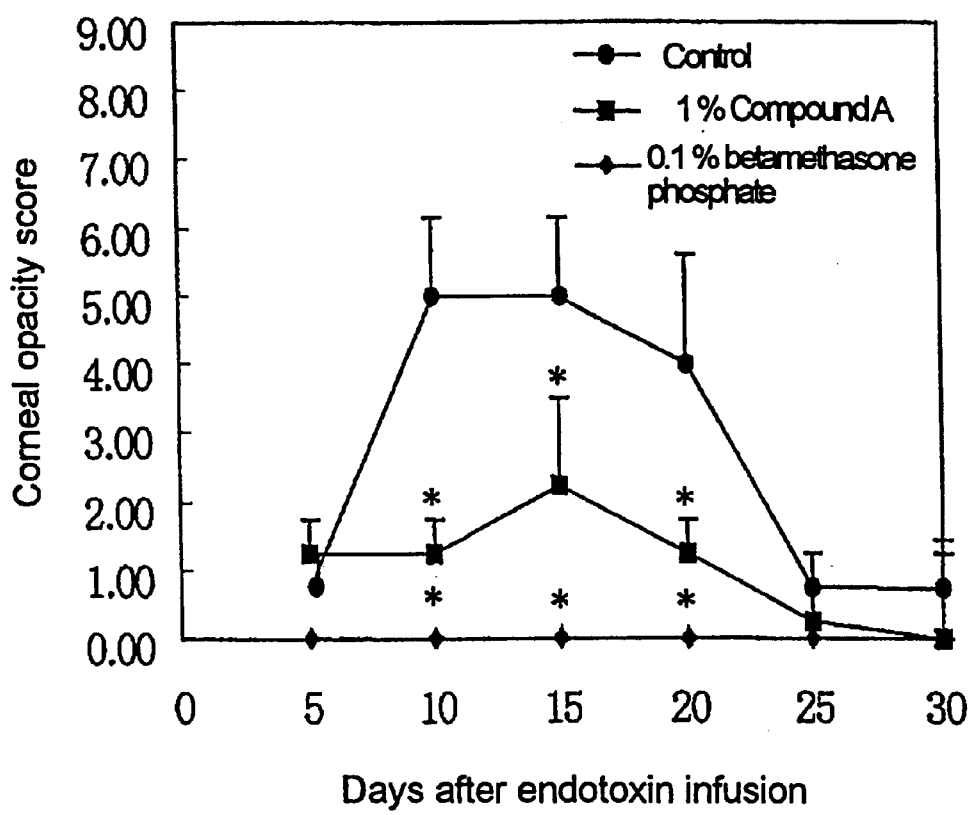
FIG. 1 is a graph showing the effect of an eye drop formulation of N-[o-(p-pivaloyloxybenzenesulfonyl-amino) benzoyl]glycine monosodium salt tetrahydrate (hereinafter referred to as Compound A) on an endotoxin-induced keratitis (effect on a corneal opacity). Each symbol represents a mean±standard deviation (n=4). A statistically significant difference from a control is analyzed with $p<0.05$ (Wilcoxon test, one-sided).

The present inventors found out that a compound represented by Formula (I) or a pharmacologically acceptable salt or hydrate thereof exhibits a marked prophylactic and therapeutic effect against various ophthalmic diseases.

Thus, the present invention provides a prophylactic and therapeutic medicament for ophthalmic diseases, especially ophthalmic inflammatory diseases and corneal ulcer, comprising as an active ingredient a compound represented by Formula (I) or a pharmacologically acceptable salt or hydrate thereof.

The present invention also provides a method for preventing and treating an ophthalmic disease which comprises administering an active ingredient mentioned above to a mammal in need of a treatment for such ophthalmic disease.

Furthermore, the present invention provides use of an active ingredient mentioned above in the manufacture of a prophylactic and therapeutic medicament for ophthalmic diseases.

Moreover, the present invention provides an eye drop formulation in the form of an aqueous suspension of an active ingredient described above.

DETAILED DESCRIPTION OF THE INVENTION

The prophylactic and therapeutic medicament according to the present invention is preferably in a dosage form for a local administration such as an eye drop formulation or an ophthalmic ointment, which is useful for preventing and treating various ophthalmic diseases such as ophthalmic infections (for example, corneal herpes, bacterial keratitis, bacterial conjunctivitis, mycotic keratitis, acanthamebic keratitis, infectious endophthalmitis, infectious corneal ulcer and the like), corneal trauma, cicatricial keratonjun ctival diseases (for example, alkaline erosive keratoconjunctivitis, Stevens-Johnson syndrome, ophthalmic pemphigoid and the like), corneal ulcer (for example, Mooren's ulcer, corneal ulcer subsequent to chronic rheumatoid arthritis or collagen disease, Terrien's margine degeneration, catarrhal corneal ulcer, infectious corneal ulcer and the like), vitamin A insufficiency-induced keratomalacia, necrotic keratitis, neuroparalytic keratitis, diabetic keratophathy, keratoconjunctiva sicca, contact lens-induced keratoconjunctivitis, vernal conjunctivitis, allergic conjunctivitis, uveitis, Behcet's syndrome, inflammation after cataract surgery and pseudopterygium, especially a keratoconjunctival inflammatory disease (for example, corneal herpes, bacterial keratitis, bacterial conjunctivitis, mycotic keratitis, acanthamebic keratitis, corneal trauma, alkaline erosive keratoconjunctivitis, corneal ulcer, vitamin A insufficiency-induced keratomalacia, necrotic keratitis, neuroparalytic keratitis, diabetic keratophathy, keratoconjunctiva sicca, contact lens-induced keratoconjunctivitis, vernal conjunctivitis, allergic conjunctivitis and the like). It is useful also for preventing and treating corneal ulcer (including various corneal ulcers described above and those induced otherwise), especially an infectious corneal ulcer.

A compound of Formula (I) used as an active ingredient according to the present invention or a pharmacologically acceptable salt thereof is a known compound described in JP-B 5-81586, and can be produced, in accordance with the procedure described therein, by the amidation of p-pivaloyloxybenzenesulfonyl chloride followed by the conversion into a salt by a known method. The resultant compound may also be converted into a hydrate by a known method.

A pharmacologically acceptable salt of a compound of Formula (I) may for example be an inorganic salt such as hydrochloride, hydrobromide, hydroiodide, sulfate, phosphate and nitrate, an organic salt such as acetate, lactate, tartarate, benzoate, citrate, methanesulfonate, ethanesulfonate, benzenesulfonate, toluenesulfonate, isethionate, glucuronate and gluconate, an alkaline metal salt (sodium salt, potassium salt and the like), an alkaline earth metal salt (calcium salt, magnesium salt and the like), an ammonium salt, a pharmacologically acceptable amine salt (tetramethylammonium salt, triethylamine salt, methylamine salt, dimethylamine salt, cyclopentylamine salt, benzylamine salt, phenethylamine salt, piperidine salt, monoethanolamine salt, diethanolamine salt, tris(hydroxymethyl) aminomethane salt, lysine salt, arginine salt, N-methyl-D-glucamine salt and the like).

One preferred especially as an active ingredient used in the present invention is a sodium salt tetrahydrate of a compound of Formula (I), i.e., N-[o-(p-pivaloyloxybenzenesulfonylamino)benzoyl]glycine monosodium salt tetrahydrate (described in Example 3 in JP-A 5-194366 corresponding to EP-A 539223) represented by Formula (I-A):

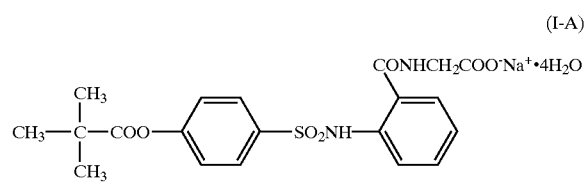

The prophylactic and therapeutic medicament for ophthalmic diseases according to the present invention, on the basis of its leukocyte-derived elastase inhibitory activity, is useful in preventing and treating various ophthalmic diseases such as an ophthalmic infections (for example, corneal herpes, bacterial keratitis, bacterial conjunctivitis, mycotic keratitis, acanthamebic keratitis, infectious endophthalmitis, infectious corneal ulcer and the like), corneal trauma, cicatricial keratoconjunctival diseases (for example, alkaline erosive keratoconjunctivitis, Stevens-Johnson syndrome, ophthalmic pemphigoid and the like), corneal ulcer (for example, Mooren's ulcer, corneal ulcer subsequent to chronic rheumatoid arthritis or collagen disease, Terrien's margine degeneration, catarrhal corneal ulcer, infectious corneal ulcer and the like), vitamin A insufficiency-induced keratomalacia, necrotic keratitis, neuroparalytic keratitis, diabetic keratophathy, keratoconjunctiva sicca, contact lens-induced keratoconjunctivitis, vernal conjunctivitis, allergic conjunctivitis, uveitis, Behcet's syndrome, inflammation after cataract surgery and pseudopterygium, especially a keratoconjunctival inflammatory disease (for example, corneal herpes, bacterial keratitis, bacterial conjunctivitis, mycotic keratitis, acanthamebic keratitis, corneal trauma, alkaline erosive keratoconjunctivitis, corneal ulcer, vitamin A insufficiency-induced keratomalacia, necrotic keratitis, neuroparalytic keratitis, diabetic keratophathy, keratoconjunctiva sicca, contact lens-induced keratoconjunctivitis, vernal conjunctivitis, allergic conjunctivitis and the like). It is useful also for preventing and treating corneal ulcer (including various corneal ulcers described above and those induced otherwise), especially infectious corneal ulcer.

The prophylactic and therapeutic medicament for ophthalmic diseases according to the present invention can be mixed with a pharmacologically acceptable carrier, excipient or diluent which is known per se and formulated by a method known per se into a pharmaceutical or a veterinary medicine in various oral or parenteral dosage forms such as tablets, capsules, granules, injection solutions, eye drops and ophthalmic ointments, and it is especially preferred to be used in a local dosage form, preferably an eye drop formulation or an ophthalmic ointment.

The eye drop formulation may for example be aqueous formulations such as aqueous eye drops, aqueous suspension eye drops, viscous eye drops and solubilized eye drops as well as non-aqueous formulations such as non-aqueous eye drops and non-aqueous suspension eye drops, with an aqueous formulation being preferred. One preferred especially is an aqueous suspension eye drop formulation.

The aqueous eye drop formulation may contain various additives incorporated ordinarily, such as buffering agents (e.g., phosphate buffers, borate buffers, citrate buffers, tartarate buffers, acetate buffers, amino acids, sodium acetate, sodium citrate and the like), isotonicities (e.g., saccharides such as sorbitol, glucose and mannitol, polyhydric alcohols such as glycerin, concentrated glycerin, polyethylene glycol and propylene glycol, salts such as sodium chloride), preservatives or antiseptics (e.g., benzalkonium chloride, benzethonium chloride, p-oxybenzoates such as methyl p-oxybenzoate or ethyl p-oxybenzoate, benzyl alcohol, phenethyl alcohol, sorbic acid or its salt, thimerosal, chlorobutanol and the like), solubilizing aids or stabilizing agents (e.g., cyclodextrins and their derivative, water-soluble polymers such as polyvinyl pyrrolidone, surfactants such as polysorbate 80 (Tween 80)), pH modifiers (e.g., hydrochloric acid, acetic acid, phosphoric acid, sodium hydroxide, potassium hydroxide, ammonium hydroxide and the like), thickening agents (e.g., hydroxyethyl cellulose, hydroxypropyl cellulose, methyl cellulose, hydroxypropylmethyl cellulose, carboxymethyl cellulose and their salts), chelating agents (e.g., sodium edetate, sodium citrate, condensed sodium phosphate) and the like.

The eye drop formulation in the form of an aqueous suspension may also contain suspending agents (e.g., polyvinyl pyrrolidone, glycerin monostearate) and dispersing agents (e.g., surfactants such as tyloxapol and polysorbate 80, ionic polymers such as sodium alginate) in addition to the additives listed above, whereby ensuring that the eye drop formulation is a further uniform microparticulate and satisfactorily dispersed aqueous suspension.

When the eye drop formulation in the form of an aqueous suspension is produced, it is preferable to use a pH modifier to make the formulation acidic pH (pH4 to 5.5). A preferred pH modifier is hydrochloric acid.

The eye drop formulation in the form of an aqueous suspension preferably contains sodium citrate or sodium acetate as a buffering agent, concentrated glycerin and/or propylene glycol as an isotonicity and polyvinyl pyrrolidone as a suspending agent. A preferred dispersing agent is a surfactant and/or sodium alginate. Such surfactant is preferably tyloxapol or polysorbate 80.

The ophthalmic ointment may employ an ointment base known per se, such as purified lanolin, petrolatum, plastibase, liquid paraffin, polyethylene glycol and the like.

The prophylactic and therapeutic medicament of the present invention may be administered to a mammal which is or may be suffered from an ophthalmic disease (e.g., human, rabbit, dog, cat, cattle, horse, monkey). While the administration route and the dose may vary depending on a symptom, age and body weight of a subject, the concentration is about 0.001 to 5 (w/v) %, preferably about 0.01 to 3 (w/v) % as a free form of a compound of Formula (I) contained in an aqueous eye drop formulation when given to an adult, and is given preferably 1 to 8 times a day with a single dose being one to several drops.

When given as the ophthalmic ointment, the dose is about 0.001 to 5 (w/v) %, preferably about 0.01 to 3 (w/v) % as a free form of a compound of Formula (I), and is given preferably 1 to 4 times a day as appropriate in view of the symptom.

Unless the intended purpose of use is affected adversely, the prophylactic and therapeutic medicament of the present invention may contain or may be used together with other appropriate pharmacologically effective substances, for example, steroidal anti-inflammatory agents (dexamethasone, prednisolone and the like), non-steroidal anti-inflammatory agents (diclofenac sodium, pranoprofen and the like), antiallergic agents (tranilast, ketotifen fumarate, sodium cromoglicate and the like), antihistamic agents (diphenhydramine hydrochloride and the like), glaucoma-treating agents (pilocarpine hydrochloride, physostigmine salicylate, timolol, isopropylunoprostone and the like), antibiotics (gentamycin sulfate, fradiomycin sulfate, tobramycin, sulbenicillin, cefmenoxime, erythromycin, colistin, oxytetracycline, polymyxin B, chloramphenicol, micronomicin, dibekacin, sisomicin and the like), antibacterial agents (sulfamethizole, sulfamethoxazole, ofloxacin, norfloxacin, lomefloxacin hydrochloride, enoxacin, ciprofloxacin hydrochloride, cinoxacin, sparfloxacin, tosufloxacin tosylate, nalidixic acid, pipemidic acid trihydrate, pipemidic acid, fleroxacin, levofloxacin and the like), and antiviral agents (idoxuridine, acyclovir and the like), and antimycotic agents (pimaricin, fluconazole, miconazole, amphotericin B, flucytosine, itraconazole and the like).

The prophylactic and therapeutic medicament of the present invention is used preferably together with at least one selected from the antibiotic, antibacterial, antiviral and antimycotic agents listed above in prophylaxis or therapy especially for an ophthalmic infection-induced inflammation or corneal ulcer. In such case, any of the antibiotic, antibacterial, antiviral and antimycotic agents can be combined with the prophylactic and therapeutic medicament of the present invention in a single formulation, or may be instilled separately. When being instilled separately, the prophylactic and therapeutic medicament of the present invention may be instilled simultaneously with any of the antibiotic, antibacterial, antiviral and antimycotic agents, or successively at a certain interval. When being instilled simultaneously, any of the prophylactic and therapeutic medicament of the present invention and the antibiotic, antibacterial, antiviral and antimycotic agents is first instilled and then preferably after a certain time period another agent is instilled whereby avoiding any escape of the agent given previously. Any of the antibiotic, antibacterial, antiviral and antimycotic agents listed above may also be given systemically by means of an oral or intravenous formulation.

The present invention is further illustrated in detail by the following Experiments and Examples, which are not construed to limit the scope of the present invention.

EXPERIMENT 1

The effect of Compound A on an ophthalmic inflammatory disease was investigated as described below.

The effect of Compound A when given as eye drops was investigated in a rabbit keratitis model using an endotoxin derived from Pseudomonas aeruginosa detected frequently in an ophthalmic infection as well as in a rabbit corneal alkaline erosion model.

Materials and Methods

(1) Animals

Male Japanese albino rabbits each weighing about 2 to 2.5 kg purchased from FUKUZAKI rabbit-raising association were used. Each animal was maintained at a temperature of 24±4° C. and a humidity of 55±15%.

(2) Test Substances

Compound A was given as a 1.0% Compound A eye drop formulation prepared by suspending Compound A in a formulation base (0.1% $NaH_2PO_4$, 0.1% polysorbate 80 and 0.9% NaCl, pH 5.0). As a positive control, a 0.1% betamethasone eye drop formulation (Rinderon™ solution, Sionogi) was used. In a control group, the formulation base was given.

(3) Methods

1) Effect on Endotoxin-induced Keratitis

16 Male Japanese albino rabbits each weighing 2 to 2.5 kg were used. The rabbits were divided into four groups each having 4 animals, which were anesthetized systemically by an intramuscular administration each of 1 ml/kg of an equal volume mixture of 5% ketamine hydrochloride and 2% xylazine hydrochloride. Each 10 µl of a 1% solution of Pseudomonas aeruginosa-derived endotoxin in physiological saline was infused into each corneal stroma of a rabbit. An anterior part of an eye was observed using a slit lamp every 5 days over a period from the day after the endotoxin infusion through the 30th day, and examined for the corneal opacity, the corneal ulcer and the vascularization, which were scored in accordance with the criteria shown in Table 1. Each test substance was started to be instilled immediately after the endotoxin infusion, and then given 4 times a day in the volume of 20 µl every 2 hours.

2) Effects on Alkaline Erosive Keratitis

16 Male Japanese albino rabbits each weighing 2 to 2.5 kg were used. The rabbits were divided into four groups each having 4 animals, which were anesthetized systemically by an intramuscular administration each of 1 ml/kg of an equal volume mixture of 5% ketamine hydrochloride and 2% xylazine hydrochloride and also locally by an instillation of oxybuprocaine hydrochloride. A filter paper whose diameter was 10 mm and which had been immersed in 2N NaOH was brought into contact with the center of the right cornea of a rabbit for 1 minute to establish an alkaline erosion, and then the eye was rinsed immediately with 10 mL or more of physiological saline. The depth of the corneal ulcer and the vascularization were observed using a slit lamp every 5 days over a period from 5 days after the alkaline erosion through the 30th day, and scored in accordance with the criteria shown in Table 1. Each test substance was started to be instilled immediately after the alkaline erosion, and then given 4 times a day in the volume of 20 µl every 2 hours.

Table 1
Rabbit Keratitis Scoring Criteria

Figure 2:
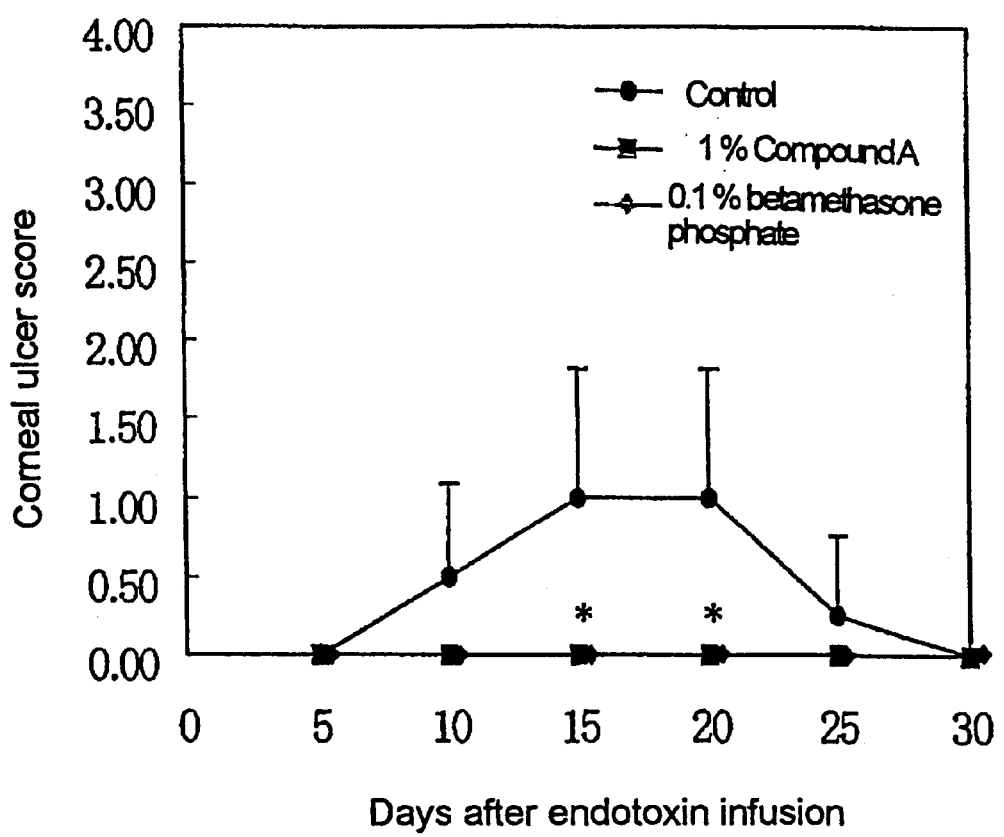
FIG. 2 is a graph showing the effect of a Compound A eye drop formulation on an endotoxin-induced keratitis (effect on a corneal ulcer). Each symbol represents a mean±standard deviation (n=4). A statistically significant difference from a control is analyzed with $p<0.05$ (Wilcoxon test, one-sided).
Figure 3:
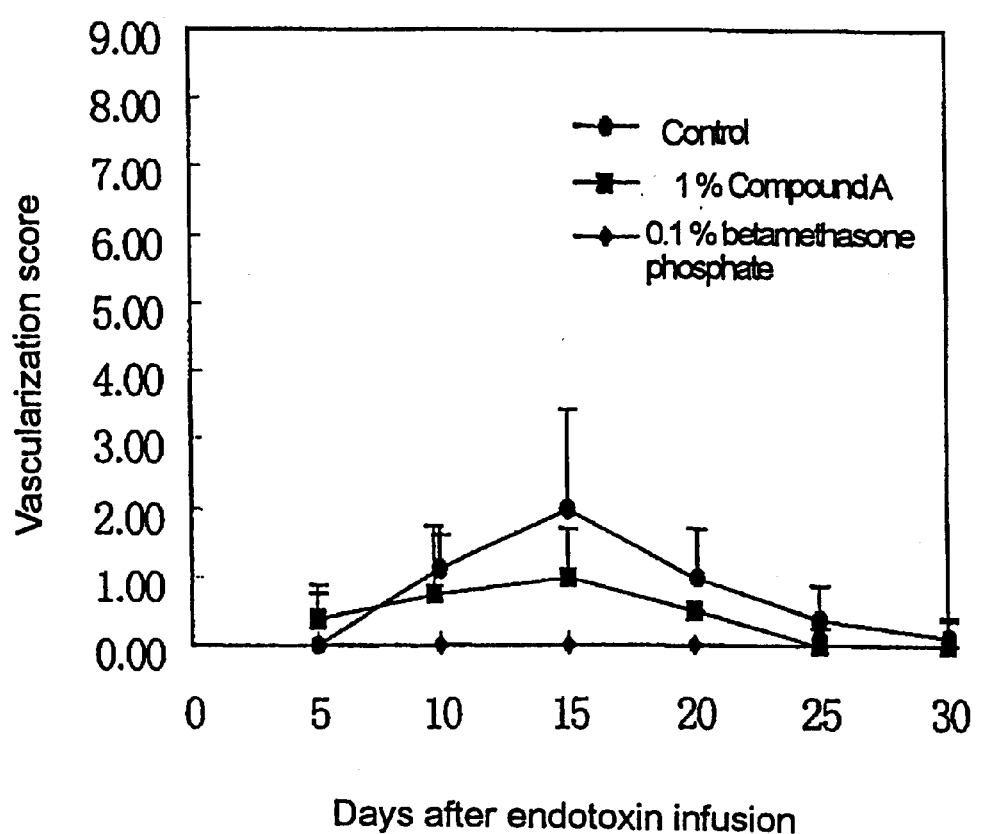
FIG. 3 is a graph showing the effect of a Compound A eye drop formulation on an endotoxin-induced keratitis (effect on a vascularization). Each symbol represents a mean±standard deviation (n=4).
Figure 4:
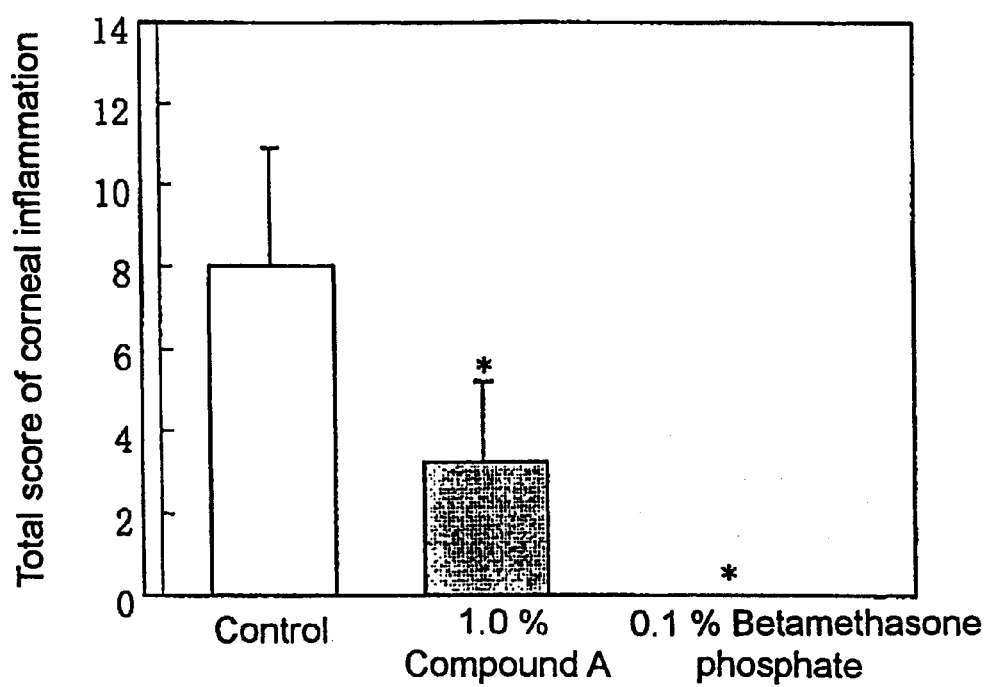
FIG. 4 shows the effect of a Compound A eye drop formulation 15 days after the challenge on an endotoxin-induced keratitis. Each column represents a mean±standard deviation (n=4). A statistically significant difference from a control is analyzed with $p<0.05$ (Wilcoxon test, one-sided).

Corneal opacity[remarks 1]
A) Degree
0: No opacity
1: Mild opacity but distinguishable anterior chamber
2: Difficulty in distinguishing details of iris
3: Almost no transparency in anterior chamber
B) Corresponding size of corneal region
1: ⅓ or less of entire
2: ⅓ to ⅔ of entire
3: ⅔ or more of entire
* Corneal ulcer
0: No corneal ulcer
1: Ulcer of less than ⅓ in depth from corneal surface toward inside of anterior chamber
2: Ulcer of ⅓ or more and less than ⅔ in depth from corneal surface toward inside of anterior chamber
3: Ulcer of ⅔ or more in depth from corneal surface toward inside of anterior chamber
4: Perforation in cornea
* Vascularization[remarks 1]
A) Length
0: No vascularization into cornea
1: Less than ⅓ from corneal limbus through center
2: Less than ⅔ from corneal limbus through center
3: ⅔ or more from corneal limbus through center
B) Region
0.5: Less than ⅓ of corneal circumference
1: ⅓ or more and less than ⅔ of corneal circumference
2: ⅔ or more of corneal circumference Remarks 1) Each as score A x score B Results and Discussion 1) Effects on Endotoxin-induced Keratitis FIGS. 1 to 3 show the change in the keratitis symptoms over a period from 5 to 30 days after the endotoxin infusion. In the control group, the severity of each symptom peaked on the 15th day, and then a gradual recovery was observed until the 30th day when almost all disappeared. In Compound A instillation group, inhibitory effects were observed on all of the evaluation items, i.e., the corneal opacity, the corneal ulcer and the vascularization, when compared with the control group. In the 0.1% betamethasone phosphate instillation group used as the positive control, the onset of the keratitis was inhibited almost completely over the observation period. FIG. 4 shows the total score in each group on the 15th day when the severity of each symptom peaked, and revealed that the % inhibition in the Compound A instillation group when compared with the control group was 59.4%, with a statistically significant difference.

Based on the results described above, the Compound A eye drop formulation was proven to be effective against various symptoms of the keratitis during an ophthalmic infection.

While betamethasone phosphate used here as a positive control exhibited an extremely potent anti-inflammatory activity, its use is limited frequently in view of a side effect experienced as the exacerbation of an infection over a prolonged therapy with a steroid in a clinical case of the ophthalmic infections.

Accordingly, the Compound A eye drop formulation expected to have a less risk of the exacerbation of an infection can serve as a hopeful agent against the ophthalmic infections.

2) Effects on Alkaline Erosive Keratitis

Figure 5:
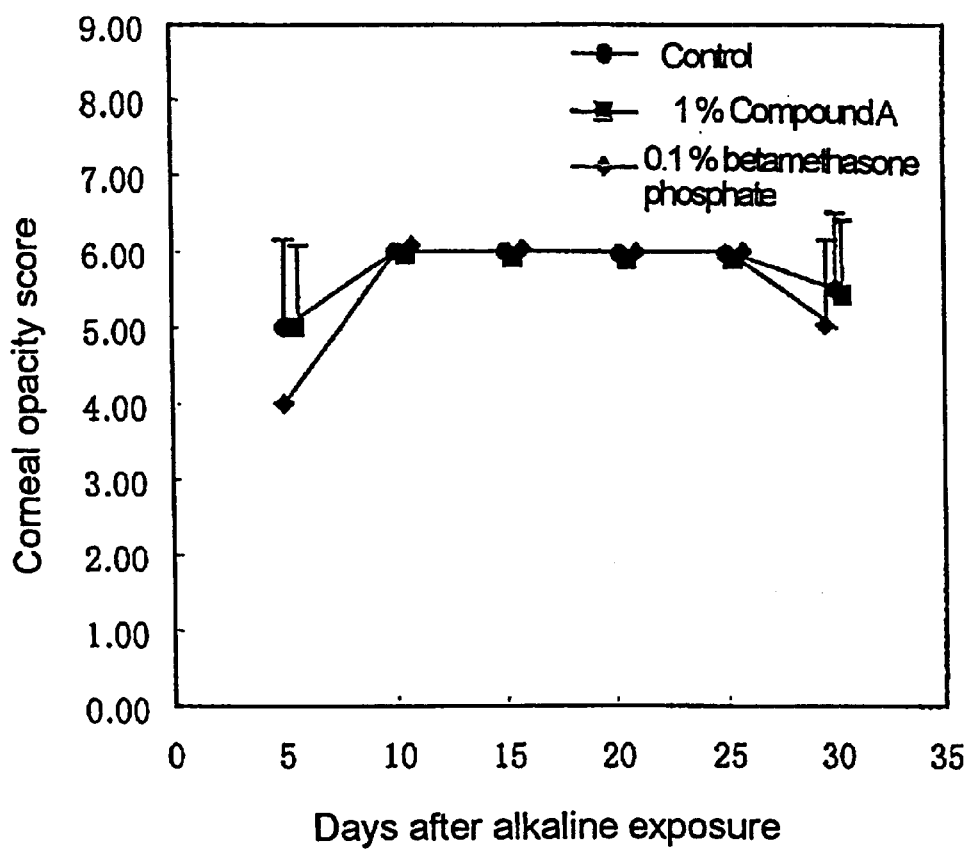
FIG. 5 is a graph showing the effect of a Compound A eye drop formulation on an alkaline erosion keratitis (effect on a corneal opacity). Each symbol represents a mean±standard deviation (n=4).
Figure 6:
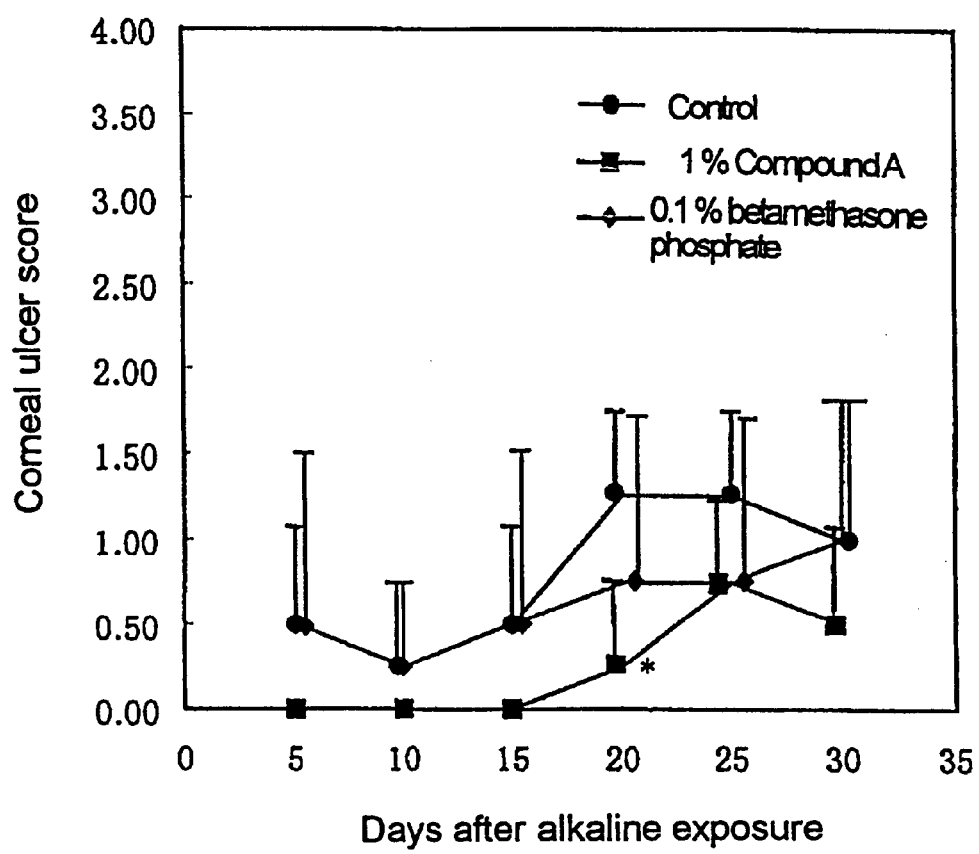
FIG. 6 is a graph showing the effect of a Compound A eye drop formulation on an alkaline erosion keratitis (effect on a corneal ulcer). Each symbol represents a mean±standard deviation (n=4). A statistically significant difference from a control is analyzed with $p<0.05$ (Wilcoxon test, one-sided).
Figure 7:
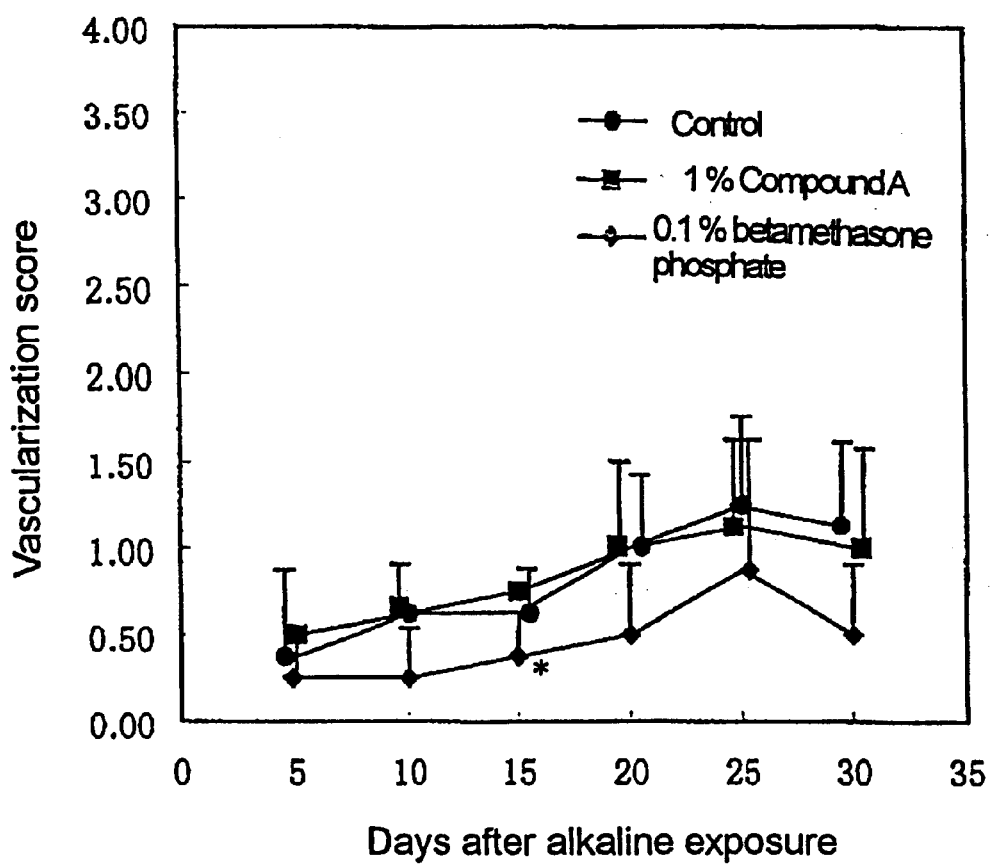
FIG. 7 is a graph showing the effect of a Compound A eye drop formulation on an alkaline erosion keratitis (effect on a vascularization). Each symbol represents a mean±standard deviation (n=4).

FIGS. 5 to 7 show the change in the keratitis symptoms over a period from 5 to 30 days after the corneal alkaline exposure. In the control group, the severity peaked on the 20 to 25th day after the corneal alkaline exposure. In Compound A instillation group, a significant inhibitory effect on the corneal ulcer was observed on the 20th day, but no effects were noted on the vascularization or the corneal opacity. In the 0.1% betamethasone phosphate instillation group used as the positive control, a significant inhibitory effect was observed on the vascularization on the 15th day.

EXPERIMENT 2

Materials and Methods (1) Animals

Male Japanese albino rabbits each weighing about 2 kg purchased from KITAYAMA LABE S CO., LTD. were used. Each animal was maintained at a temperature of 23±3° C. and a humidity of 55±10%.

(2) Test Substances

Compound A was given as a 1.0% Compound A eye drop formulation prepared by suspending Compound A in a formulation base (0.1% sodium acetate, 0.1% polysorbate 80 and 0.9% NaCl, pH 5.0). A 0.3% lomefloxacin (LFLX) hydrochloride was used as an. is antibacterial agent, and physiological saline *was used as a control.

(3) Methods

1) Excision of Nictitating Membrane

After instilling 0.4% oxybuprocaine hydrochloride for a local anesthesia, a nictitating membrane was excised.

2) Inoculation

A causative microorganism used was a clinical isolate Pseudomonas aeruginosa strain No. ho-134. A rabbit was anesthetized systemically with 5% ketamine hydrochloride and 2% xylazine hydrochloride (equal volume mixture), and then inoculated by an infusion of 30 µl of a $3.9 \times 10^4$ CFU/ml cell suspension ($1.17 \times 10^3$ CFU/cornea) using a 100 µl microsyringe fitted with a 30G needle into one corneal stroma of a rabbit.

3) Instillation

An animal which had received an infusion of the cell suspension into the corneal stroma and whose inoculation was surely successful was grouped into one of [1] physiological saline instillation group (control, n=6) and [2]1.0% Compound A instillation group (Compound A group, n=6) as groups whose therapy was started immediately after the inoculation, and [3]1.0% Compound A instillation group (late Compound A group, n=5), [4]0.3% LFLX instillation group (LFLX group, n=6) and [5]1.0% Compound A instillation—0.3% LFLX instillation combination group (Compound A—LFLX combination group, n=6) as groups whose therapy was started 1 day after the inoculation (after onset of corneal ulcer), and 50 µl of each substance was given four times a day immediately after the inoculation or 1 day after the inoculation (after onset of corneal ulcer). In the Compound A—LFLX combination group, the 1.0% Compound A eye drop formulation was instilled about 10 minutes after the instillation of the 0.3% LFLX eye drop formulation.

4) Observation of Infectious Symptoms

Each animal was examined for the corneal ulcer every 24 hours after the inoculation and scored in accordance with the rabbit corneal lesion scoring criteria (Barletta J. P. et al., Invest Ophthalmol Vis Sic 37:20–28, 1996) shown in Table 2.

Table 2
Rabbit Corneal Lesion Scoring Criteria

* Corneal ulcer

0:No corneal ulcer

1:Ulcer of less than ¼ of entire cornea

2:Ulcer of ¼ or more and less than ½ of entire cornea

3:Ulcer of ½ or more and less than ¾ of entire cornea

4:Ulcer of ¾ or more of entire cornea

Results and Discussion

Figure 8:
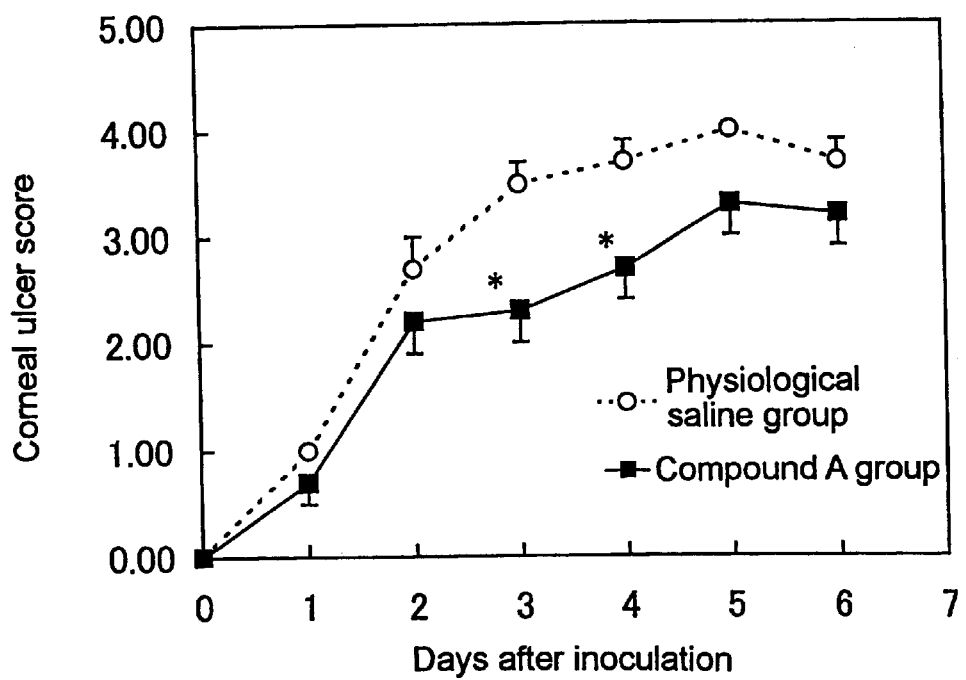
FIG. 8 is a graph showing the effect of a Compound A eye drop formulation on a pyocyanic corneal ulcer immediately after the inoculation of the microbe. Each symbol represents a mean±standard deviation (n=6). A statistically significant difference from a control is analyzed with $p<0.05$ (Wilcoxon test, one-sided).

1) Effects on Pyocyanic Corneal Ulcer—Effect of Instillation Started Immediately After Inoculation The results of the instillation started immediately after the inoculation are shown in FIG. 8. The corneal ulcer was exacerbated gradually in the control group (physiological saline group) toward an extensive corneal ulcer 5 days after the inoculation. On the contrary, the corneal ulcer formation was started to be inhibited 3 days after the inoculation in the Compound A group, with a statistically significant difference (FIG. 8).

Figure 9:
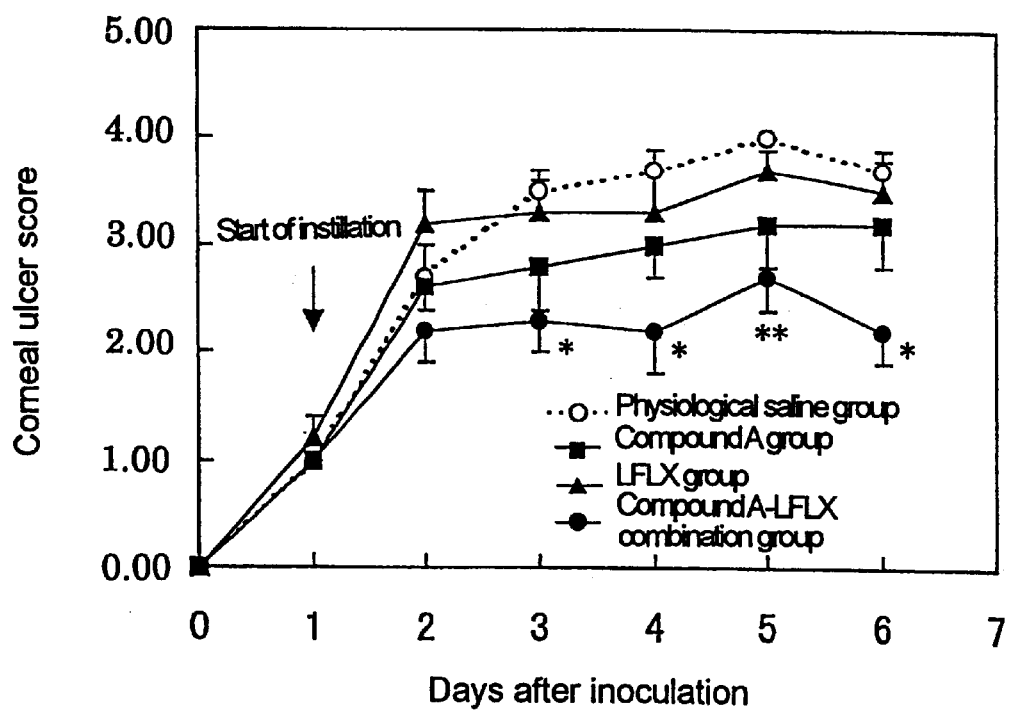
FIG. 9 is a graph showing the effects of the instillation of Compound A and lomefloxacin on a pyocyanic corneal ulcer one day after the inoculation of the microbe and later. Each symbol represents a mean±standard deviation (n=5–6). A statistically significant difference from a control is analyzed with * $p<0.05$ and ** $p<0.01$ (Steel test, one-sided).

2) Effects on Pyocyanic Corneal Ulcer—Effect of Instillation Started One Day After Inoculation In the late Compound A group in which the instillation was started 1 day after the inoculation, the corneal ulcer formation was started to be inhibited 3 days after the inoculation. The LFLX group exhibited the change similar to that in the control group, with no inhibition of the corneal ulcer formation being noted (FIG. 9). In the Compound A—LFLX combination group, the corneal ulcer formation was started to be inhibited potently 3 days after the inoculation, with a statistically significant difference (FIG. 9).

Based on the results observed as described above, Compound A as an elastase inhibitor was proven to be effective against the corneal ulcer induced by bacterial infection. It was also proven that a combination of an elastase inhibitor with an antibacterial agent was more markedly effective against the corneal ulcer of a bacterial infection than each agent used alone.

EXAMPLE 1

An aqueous eye drop formulation was prepared using the following composition.

| Component | Quantity |
| --- | --- |
| Compound A | 0.1 g |
| Sodium chloride | 0.9 g |
| Sodium acetate | 0.1 g |
| Benzalkonium chloride | 0.005 g |
| Hydrochloric acid | As appropriate |
| Sodium hydroxide | As appropriate |
| Sterilized purified water | to 100 mL (pH 6.0) |

In about 80 ml of purified water, Compound A, sodium chloride, sodium acetate and benzalkonium chloride were dissolved. The solution was adjusted at pH 6.0 using hydrochloric acid and sodium hydroxide. Sterilized purified water was added to make the entire volume 100 mL, whereby obtaining an aqueous eye drop formulation.

EXAMPLE 2

An eye drop formulation as an aqueous suspension was prepared using the following composition.

| Component | Quantity |
| --- | --- |
| Compound A | 1.0 g |
| Sodium chloride | 0.9 g |
| Sodium acetate | 0.1 g |
| Polysorbate 80 | 0.2 g |
| Benzalkonium chloride | 0.005 g |
| Hydrochloric acid | As appropriate |
| Sodium hydroxide | As appropriate |
| Sterilized purified water | to 100 mL (pH 5.0) |

In about 80 ml of purified water, sodium chloride, sodium acetate, polysorbate 80 and benzalkonium chloride were dissolved. The solution was adjusted at pH 5.0 using hydrochloric acid and sodium hydroxide, and then Compound A was added and suspended uniformly using a homogenizer.

Sterilized purified water was added to make the entire volume 100 mL, whereby obtaining an eye drop formulation as an aqueous suspension.

EXAMPLE 3

An eye drop formulation as an aqueous suspension was prepared using the following composition.

| Component | Quantity |
| --- | --- |
| Compound A | 0.5 g |
| Concentrated glycerin | 2.6 g |
| Sodium acetate | 0.1 g |
| Hydroxypropylmethyl cellulose | 0.2 g |
| Methyl p-oxybenzoate | 0.03 g |
| Propyl p-oxybenzoate | 0.02 g |
| Hydrochloric acid | As appropriate |
| Sodium hydroxide | As appropriate |
| Sterilized purified water | to 100 mL (pH 5.0) |

About 80 ml of purified water was warmed and methyl p-oxybenzoate and propyl p-oxybenzoate were dissolved. In this solution, hydroxypropylmethyl cellulose was dispersed and then cooled to room temperature for dissolution. To this solution, concentrated glycerin and sodium acetate were added, and then the pH was adjusted at 5.0 using hydrochloric acid and sodium hydroxide. To this solution, Compound A was added and suspended uniformly using a homogenizer. Sterilized purified water was added to make the entire volume 100 mL, whereby obtaining an eye drop formulation as an aqueous suspension.

EXAMPLE 4

The following composition was used to make an ophthalmic ointment

| Component | Quantity |
| --- | --- |
| Compound A | 2.0 g |
| Liquid paraffin | 2.0 g |
| White petrolatum | to 100 g |

Liquid paraffin and white petrolatum were sterilized previously by heating. Subsequently, Compound A was mixed thoroughly with liquid paraffin, and then kneaded with the white petrolatum to obtain an ophthalmic ointment.

EXAMPLE 5

An eye drop formulation as an aqueous suspension was prepared using the following composition.

| Component | Quantity |
| --- | --- |
| Compound A | 1.0 g |
| Sodium citrate | 0.1 g |
| Concentrated glycerin | 1.2 g |
| Methyl p-oxybenzoate | 0.026 g |
| Propyl p-oxybenzoate | 0.014 g |
| Propylene glycol | 1.0 g |
| Polyvinyl pyrrolidone (K-25) | 0.5 g |

-continued

| Component | Quantity |
| --- | --- |
| Sodium alginate | 0.2 g |
| Hydrochloric acid | As appropriate |
| Sterilized purified water | to 100 mL (pH 5.0) |

In about 80 ml of purified water, sodium citrate, concentrated glycerin, methyl p-oxybenzoate, propyl p-oxybenzoate, propylene glycol and polyvinyl pyrrolidone were dissolved. In this solution, Compound A was dissolved and the solution was filtered through a 0.22 $\mu$m membrane filter, adjusted at pH 5.0 with hydrochloric acid, whereby precipitating a fine crystal (2 to 3 $\mu$m) of Compound A. Sodium alginate was dissolved, and purified water was added to make the entire volume 100 mL, whereby obtaining an eye drop formulation as an aqueous suspension.

After a storage for 4 weeks at 60° C., the eye drop formulation as an aqueous suspension contained 101.7% of Compound A, and exhibited a satisfactory re-dispersion performance without any aggregation.

EXAMPLE 6

An eye drop formulation as an aqueous suspension was prepared using the following composition.

| Component | Quantity |
| --- | --- |
| Compound A | 1.0 g |
| Sodium citrate | 0.1 g |
| Concentrated glycerin | 1.2 g |
| Methyl p-oxybenzoate | 0.026 g |
| Propyl p-oxybenzoate | 0.014 g |
| Propylene glycol | 1.0 g |
| Polyvinyl pyrrolidone (K-25) | 0.5 g |
| Sodium alginate | 0.2 g |
| Tyloxapol | 0.1 g |
| Hydrochloric acid | As appropriate |
| Sterilized purified water | to 100 mL (pH 5.0) |

In about 80 ml of purified water, sodium citrate, concentrated glycerin, methyl p-oxybenzoate, propyl p-oxybenzoate, propylene glycol and polyvinyl pyrrolidone were dissolved. In this solution, Compound A was dissolved and the solution was filtered through a 0.22 $\mu$m membrane filter, adjusted at pH 5.0 with hydrochloric acid, whereby precipitating a fine crystal (2 to 3 $\mu$m) of Compound A. Sodium alginate and tyloxapol were dissolved, and purified water was added to make the entire volume 100 mL, whereby obtaining an eye drop formulation as an aqueous suspension.

After a storage for 2 weeks at 60° C., the eye drop formulation as an aqueous suspension contained 102.5% of Compound A, and exhibited a satisfactory redispersion performance without any aggregation.

EXAMPLE 7

An eye drop formulation as an aqueous suspension was prepared using the following composition.

| Component | Quantity |
| --- | --- |
| Compound A | 1.0 g |
| Sodium citrate | 0.1 g |
| Concentrated glycerin | 1.2 g |
| Methyl p-oxybenzoate | 0.026 g |
| Propyl p-oxybenzoate | 0.014 g |
| Polyvinyl pyrrolidone (K-25) | 0.5 g |
| Sodium alginate | 0.2 g |
| Tyloxapol | 0.1 g |
| Hydrochloric acid | As appropriate |
| Sterilized purified water | to 100 mL (pH 5.0) |

In about 80 ml of purified water, sodium citrate, concentrated glycerin, methyl p-oxybenzoate, propyl p-oxybenzoate and polyvinyl pyrrolidone were dissolved. In this solution, Compound A was dissolved and the solution was filtered through a 0.22 μm membrane filter, adjusted at pH 5.0 with hydrochloric acid, whereby precipitating a fine crystal (2 to 3 μm) of Compound A. Sodium alginate and tyloxapol were dissolved, and purified water was added to make the entire volume 100 mL, whereby obtaining an eye drop formulation as an aqueous suspension.

EXAMPLE 8

An eye drop formulation as an aqueous suspension was prepared using the following composition.

| Component | Quantity |
| --- | --- |
| Compound A | 1.0 g |
| Sodium citrate | 0.1 g |
| Concentrated glycerin | 1.2 g |
| Benzalkonium chloride | 0.005 g |
| Polyvinyl pyrrolidone (K-25) | 0.5 g |
| Sodium alginate | 0.2 g |
| Tyloxapol | 0.1 g |
| Hydrochloric acid | As appropriate |
| Sterilized purified water | to 100 mL (pH 5.0) |

In about 80 ml of purified water, sodium citrate, concentrated glycerin and polyvinyl pyrrolidone were dissolved. In this solution, Compound A was dissolved and the solution was filtered through a 0.22 μm membrane filter, adjusted at pH 5.0 with hydrochloric acid, whereby precipitating a fine crystal (2 to 3 μm) of Compound A. Sodium alginate and tyloxapol were dissolved, and then benzalkonium chloride was dissolved. Purified water was added to make the entire volume 100 mL, whereby obtaining an eye drop formulation as an aqueous suspension.

Industrial Applicability

According to the present invention, the pharmaceutical or a veterinary medicine which is effective in preventing or treating ophthalmic diseases, especially ophthalmic inflammatory diseases and corneal ulcer, can be provided.

What is claimed is:

1. A prophylactic and therapeutic medicament for ophthalmic disease in a dosage form for local administration to the eye, which comprises as an active ingredient a compound represented by the formula (I):

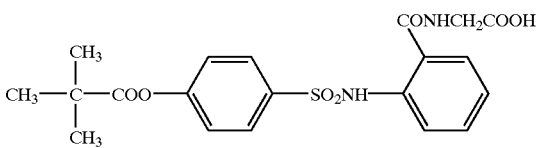

or a pharmacologically acceptable salt or hydrate thereof, together with a pharmaceutically acceptable carrier, excipient or diluent.

2. The prophylactic and therapeutic medicament according to claim 1 which is an eye drop formulation.

3. The prophylactic and therapeutic medicament according to claim 2 which is an eye drop formulation in the form of an aqueous suspension.

4. The prophylactic and therapeutic medicament according to claim 1 which is an ophthalmic ointment.

5. The prophylactic and therapeutic medicament according to claim 1 which is a prophylactic and therapeutic medicament for ophthalmic inflammatory disease.

6. The prophylactic and therapeutic medicament according to claim 5 which is a prophylactic and therapeutic medicament for keratoconjunctival inflammatory disease.

7. The prophylactic and therapeutic medicament according to claim 1 which is a prophylactic and therapeutic medicament for corneal ulcer.

8. The prophylactic and therapeutic medicament according to claim 7 which is a prophylactic and therapeutic medicament for infectious corneal ulcer.

9. A method for treating an ophthalmic disease, which comprises administering locally to an eye an effective amount of a compound represented by the formula (I):

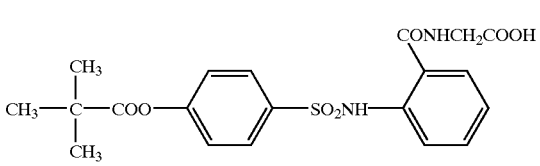

or a pharmacologically acceptable salt or hydrate thereof to a mammal in need of treatment thereof.

10. The method according to claim 9, wherein N-[o-(p-pivaloyloxybenzenesulfonylamino)benzoyl]glycine monosodium salt tetrahydrate is administered.

11. The method according to claim 9, wherein the ophthalmic disease is an ophthalmic inflammatory disease.

12. The method according to claim 11, wherein the ophthalmic inflammatory disease is a keratoconjunctival inflammatory disease.

13. The method according to claim 9, wherein the ophthalmic disease is corneal ulcer.

14. The method according to claim 13, wherein the corneal ulcer is an infectious corneal ulcer.

15. The method according to claim 9, wherein at least one of antibiotics, antibacterial agents, antiviral agents and antimycotic agents is used together.

16. An eye drop formulation comprising an aqueous suspension of a compound represented by the formula (I):

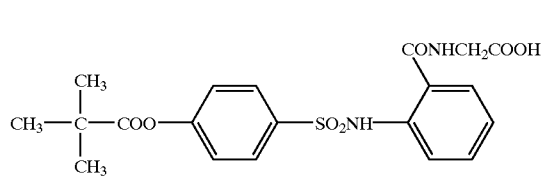

(I)

or a pharmacologically acceptable salt or hydrate thereof which is adjusted to a pH in a range of 4.0 to 5.5 using at least one pH modifier.

17. The eye drop formulation in the form of an aqueous suspension according to claim 16, wherein the pH modifier is hydrochloric acid or hydrochloric acid in combination with sodium hydroxide.

18. The eye drop formulation in the form of an aqueous suspension according to claim 16, comprising a buffering agent, an isotonicity, a suspending agent and a dispersing agent.

19. The eye drop formulation in the form of an aqueous suspension according to claim 18, wherein the buffering agent is sodium citrate or sodium acetate.

20. The eye drop formulation in the form of an aqueous suspension according to claim 18, wherein the isotonicity is concentrated glycerin and/or propylene glycol.

21. The eye drop formulation in the form of an aqueous suspension according to claim 18, wherein the suspending agent is polyvinyl pyrrolidone.

22. An eye drop formulation in the form of an aqueous suspension according to claim 18, wherein the dispersing agent is a surfactant and/or sodium alginate.

23. The eye drop formulation in the form of an aqueous suspension according to the above-mentioned claim 22 wherein the surfactant is tyloxapol or polysorbate 80.

24. A method for making an eye drop formulation or an ophthalmic ointment, which comprises mixing a compound represented by the formula (I):

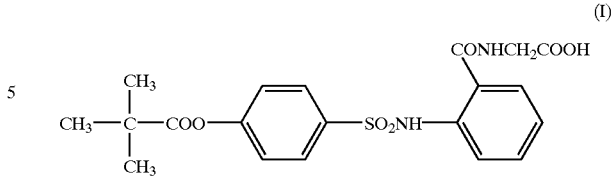

(I)

or a pharmacologically acceptable salt or hydrate thereof with a suitable pharmaceutically acceptable carrier, excipient or diluent.

25. The method according to claim 24, wherein the compound is N-[o-(p-loxybenzenesulfonylamino)benzoyl] glycine monosodium salt tetrahydrate.

26. A method of treatment for ophthalmic inflammation, which comprises administering locally to an eye an effective amount of a compound represented by the formula (I):

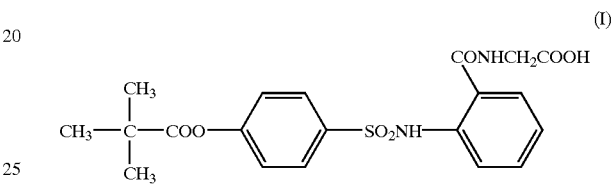

(I)

or a pharmacologically acceptable salt or hydrate thereof to a mammal in need of treatment thereof.

27. A method of treatment for corneal ulcer, which comprises administering locally to an eye an effective amount of a compound represented by the formula (I):

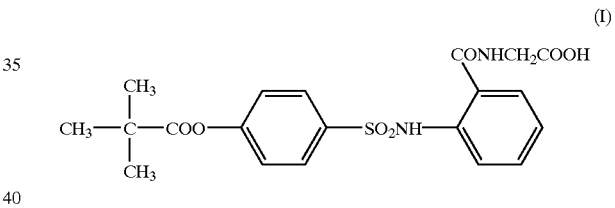

(I)

or a pharmacologically acceptable salt or hydrate thereof to a mammal in need of treatment thereof.

* * * * *